(12) United States Patent  
Henschke et al.

(10) Patent No.: US 8,168,766 B2
(45) Date of Patent: May 1, 2012

(54) PROCESS OF MAKING 2-DEOXY-2,2-DIFLUORO-D-RIBO-FURANOSYL NUCLEOSIDES AND INTERMEDIATES THEREFOR

(75) Inventors: Julian Paul Henschke, Harlow (GB); Yung Fa Chen, Tainan County (TW); George Charles Schloemer, Bradenton, FL (US)

(73) Assignee: ScnioPharm Taiwan Ltd., Tainan (TW)

( * ) Notice: Subject to any disclaimer, the term of this patent is extended or adjusted under 35 U.S.C. 154(b) by 430 days.

(21) Appl. No.: 12/550,548

(22) Filed: Aug. 31, 2009

(65) Prior Publication Data
US 2010/0056771 A1    Mar. 4, 2010

Related U.S. Application Data

(60) Provisional application No. 61/190,577, filed on Aug. 29, 2008.

(51) Int. Cl.
*C07H 13/02* (2006.01)
*C07H 13/04* (2006.01)
*C07H 13/08* (2006.01)
*C07H 5/04* (2006.01)
*C07H 19/06* (2006.01)
*C07H 19/073* (2006.01)
*C07H 19/16* (2006.01)
*C07H 19/173* (2006.01)

(52) U.S. Cl. .............. 536/17.9; 536/27.21; 536/27.23; 536/27.3; 536/28.5; 536/28.53

(58) Field of Classification Search .............. None
See application file for complete search history.

(56) References Cited

U.S. PATENT DOCUMENTS
5,223,608 A * 6/1993 Chou et al. ............... 536/28.5

OTHER PUBLICATIONS

Tsutsumi et al., "A New Method for Glycosylation With Carbodiimides; Nucleophilic Substitution of Glycosylisoureas" Chemistry Letters (1978) pp. 629-632.*
Tsutsumi et al. "Partial protection of carbohydrate derivatives. X. Synthetic studies of 5,6-dimethyl-I-(.alpha.-D-ribofuranosyl)benzimidazole" Nippon Kagakukai shi (1972) pp. 1682-1691.*
Bock et al. Synthesis and properties of 1,1,3,3,-tetramethyl-2-(2,3,4,6-tetra-Oacetyl-I±-d-glucopyranosyl) uronium triflate Carbohydrate research (1992) vol. 232 pp. 353-357.*

* cited by examiner

*Primary Examiner* — Eric S Olson

(57) ABSTRACT

A compound of formula (A) or salt thereof:

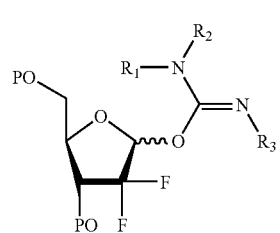

wherein each of $R_1$, $R_2$, and $R_3$ independently represents hydrogen, alkyl, aryl, acyl, sulfonyl, or silyl; P represents hydrogen or a hydroxy protective group. This compound may be used an intermediate for making a 2-deoxy-2,2-difluoro-D-ribofuranosyl nucleosides, such as gemcitabine.

19 Claims, No Drawings

PROCESS OF MAKING 2-DEOXY-2,2-DIFLUORO-D-RIBOFURANOSYL NUCLEOSIDES AND INTERMEDIATES THEREFOR

RELATED APPLICATIONS

This application claims priority from U.S. Provisional Patent Application Ser. No. 61/190,577 which was filed on Aug. 29, 2008. The entire content of this application is incorporated herein as reference.

BACKGROUND OF THE INVENTION

1. Field of the Invention

The present application relates to process of making 2-deoxy-2,2-difluoro-D-ribofuranosyl nucleosides, such as gemcitabine, intermediates therefor, and process of making the intermediates.

2. Description of the Related Art

2-Deoxy-2,2-difluoro-D-ribofuranosyl nucleosides, such as gemcitabine, have been known as therapeutic agents in viral and cancerous disease.

Processes for preparing the nucleoside agents involve the stereochemical inversion of carbohydrate intermediates bearing a leaving group at the anomeric center. Therefore, when a beta-anomer nucleoside is the desired product, an alpha-anomer enriched carbohydrate intermediate is preferably used in $S_N2$ coupling reactions.

It has been reported that sulfonate, halide, or imidate may be used as a leaving group at the anomeric center of a carbohydrate intermediates for making nucleosides. During the reaction of the carbohydrate with a nucleobase to form a nucleoside, the leaving group on the carbohydrate intermediate is displaced with a multiply silylated derivative of a nucleobase.

The reaction can proceed by either an $S_N1$ or an $S_N2$ mechanism. Without using a catalyst, the reaction is typically slow. Therefore, a catalyst (typically a Lewis acid such as TMSOTf) is often used to accelerate the reaction. The reaction normally proceeds to give a protected nucleoside product with a ratio of the alpha-anomer to the beta-anomer of approximately 1:1. If an anomerically enriched starting sugar is used and an $S_N2$ pathway is utilised, typically when a catalyst is not used, the reaction is more stereochemically selective. Nevertheless, to make a more anomerically enrich form of carbohydrate intermediate, the methods reported in the art often require additional steps and/or conditions such crystallisation or a low temperature.

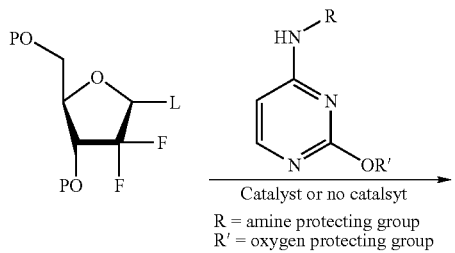
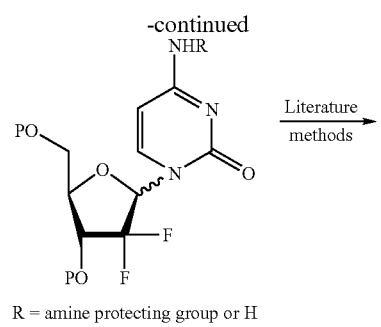

R = amine protecting group
R' = oxygen protecting group

R = amine protecting group or H

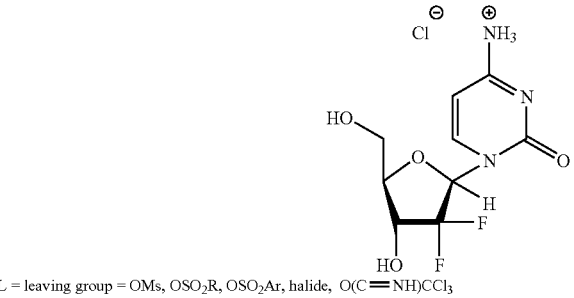

L = leaving group = OMs, OSO₂R, OSO₂Ar, halide, O(C=NH)CCl₃

There is still need for a more simple and/or efficient process for making a 2-deoxy-2,2-difluoro-D-ribofuranosyl nucleoside.

SUMMARY OF THE INVENTION

The first aspect of the present application is a compound of formula (A) or salt thereof:

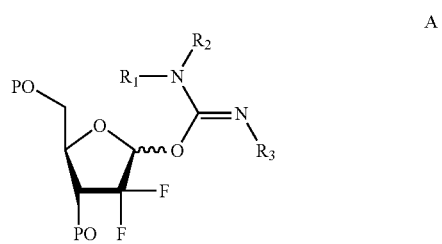

A wherein each of $R_1$, $R_2$, and $R_3$ independently represents hydrogen, alkyl, aryl, acyl, sulfonyl, or silyl; P represents hydrogen or a hydroxy protective group.

The hydroxyl protecting group involved in the present application can be any suitable group that is capable of preventing a hydroxyl group from undesired reaction. For example, the hydroxy protecting group may be benzoyl, 4-phenylbenzoyl, 4-bromobenzoyl, 4-chlorobenzoyl, formyl, acetyl, 2-chloroacetyl, benzyl, diphenylmethyl, triphenyl methyl, 4-nitrobenzyl, phenoxycarbonyl, tertiary-butyl, methoxymethyl, tetrahydropyranyl, allyl, tetrahydrothienyl, 2-methoxethoxy methyl, methoxy acetyl, phenoxy acetyl, isobutyryl, ethoxy carbonyl, benzyloxy carbonyl, mesyl, trimethylsilyl, isopropyl dimethylsilyl, methyldiisopropyl silyl, triisopropyl silyl, or tertiary-butyldimethyl silyl. As a preferred embodiment, the hydroxyl protecting group is benzoyl.

Preferably, each of $R_1$ and $R_3$ in the above formula (A) independently represents an alkyl group (including cycloalkyl) or an aryl group, and $R_2$ represents hydrogen or sulfonyl group.

Preferably, the salt of the compound of formula (A) is a compound having formula (B):

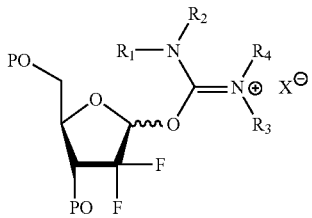

B wherein each of $R_1$, $R_2$, $R_3$, and P is as defined above; $R_4$ is hydrogen, alkyl, aryl, acyl, sulfonyl, or silyl; and X represents a non-nucleophilic counter ion. More preferably, X is halide, sulfonate, carboxylate, $^-PF_6$, or $^-BF_4$. For example, X may be perfluorosulfonate or perfluorocarboxylate.

Preferably, each of $R_1$, $R_2$, $R_3$, $R_4$ in the above formula (b) represents methyl, and X represents chloride or triflate.

The alkyl group involved in the present application is preferably $C_1$-$C_{20}$ alkyl; the aryl group is preferably $C_6$-$C_{20}$ aryl; and the acyl group is preferably $C_1$-$C_{20}$ acyl. The silyl group can be any suitable group, including those reported in the art. For example, the silyl group may be a trialkyl substituted silyl group ($alkyl_3Si$), such as trimethylsilyl, triisopropylsilyl, and triethylsilyl.

The second aspect of the present application is a process of making a compound of formula (A)

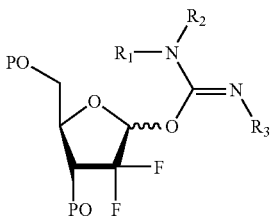

A wherein each of $R_1$, $R_2$, and $R_3$ independently represents hydrogen, alkyl, aryl, acyl, sulfonyl, or silyl; P represents hydrogen or a hydroxy protective group. The process comprises: reacting a 3,5-di-O-protected 2-deoxy-2,2-difluoro-D-ribose with a carbodiimide compound of formula C

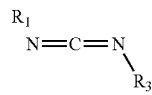

C in an organic solvent in the presence of a catalyst.

Preferably, the carbodiimide compound is a dialykicarbodiimide such as dicyclohexylcarbodiimide (DCC).

Preferably, the catalyst is a metal salt, in particular a cuprate salt.

The organic solvent may be any suitable non-reactive solvent. For example, the organic solvent may be ($C_1$-$C_2$) halogenated hydrocarbons, acetic acid, ($C_{1-4}$) alkyl esters, ($C_2$-$C_{12}$) ethers, ($C_6$-$C_9$) aromatic hydrocarbons, and combinations thereof.

Preferably, the temperature at which the reaction of the 3,5-di-O-protected 2-deoxy-2,2-difluoro-D-ribose and the carbodiimide compound of formula C is carried out depends on the specific solvent used, in particular the boiling point and melting point of the solvent. Typically, the reaction temperature is 0° C. to 100° C., more preferably, at a room temperature (i.e., around 25° C.).

When $R_2$ in the above formula (A) represents sulfonyl, the process may comprise a further step of reacting the product of the reaction of the 3,5-di-O-protected 2-deoxy-2,2-difluoro-D-ribose and the carbodiimide compound of formula C with a sulfonating agent in an organic solvent in the presence of an amine base. Preferably, the sulfonating agent is a sulfonic anhydride or sulfonyl halide; the amine base is triethylamine ($Et_3N$) or N,N-diisopropylethylamine (DIPEA). An additional base such as 4-(N,N-dimethylamino)pyridine (DMAP) can also be used in substoichiometric amounts.

When a salt of the compound of formula (A) is to be produced, the process comprises a further step of converting the reaction product of the 3,5-di-O-protected 2-deoxy-2,2-difluoro-D-ribose and the carbodiimide compound of formula C to the salt of the compound of formula (A). For example, the reaction product of the 3,5-di-O-protected 2-deoxy-2,2-difluoro-D-ribose and the carbodiimide compound of formula C may react with an activating agent or alkylating agent to produce the salt of the compound of formula (A). As shown in the scheme below, the activating agent may be a Brønsted acid (for example TfOH, i.e., triflic acid) or a Lewis acid (for example TMSOTf, i.e., trimethylsilyl trifluoromethylsulfonate). The alkylating agent may be an alkyl sulfonate or alkyl halide.

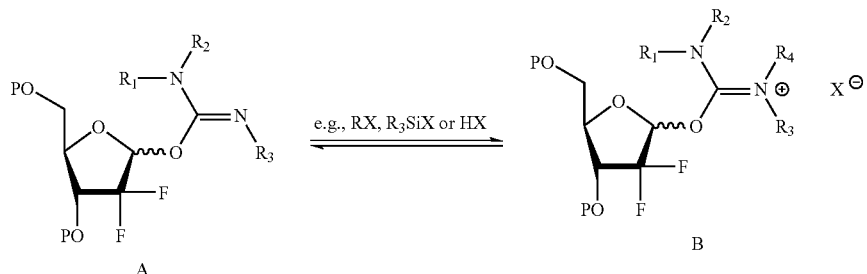

$R_4$ = H, alkly or $SiR_3$
X = halide, sulphonate etc.

The third aspect of the present application is a process of making a compound of formula B

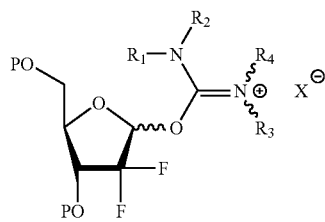

B wherein each of $R_1$, $R_2$, $R_3$, $R_4$ is independently alkyl or aryl; and P is hydrogen or a hydroxyl protecting group; and X represents a non-nucleophilic counter ion. The process comprises:
reacting a 3,5-di-protected 2-deoxy-2,2-difluoro-D-ribose with an activated urea-derived compound having a formula D

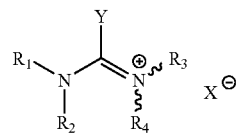

D where each of $R_1$, $R_2$, $R_3$, $R_4$, and X is defined as above, Y is selected from the group consisting of halo, sulfonate, carboxylate, and trifluoromethanesulfonate in an organic solvent in the presence of a non-nucleophilic amine base. Preferably, the non-nucleophilic amine base is $Et_3N$ or DIPEA. The reacting step may be carried out at a temperature of $-80°$ C. to $40°$ C.

The organic solvent may be any suitable non-reactive solvent, such as ethers ($Et_2O$, THF, MTBE etc.), aromatics (toluene, xylenes etc.), ketones (acetone, MIBK etc.) More specifically, the organic solvent may be dichloromethane (DCM) or 1,2-dichloroethane (DCE).

The product obtained in this process may be purified by aqueous washing and/or crystallization.

The activated urea-derived compound of formula (D) may be prepared by any suitable method. For example, it may be readily synthesized from a urea compound and an electrophile, such as oxaloyl chloride and triflic anhydride.

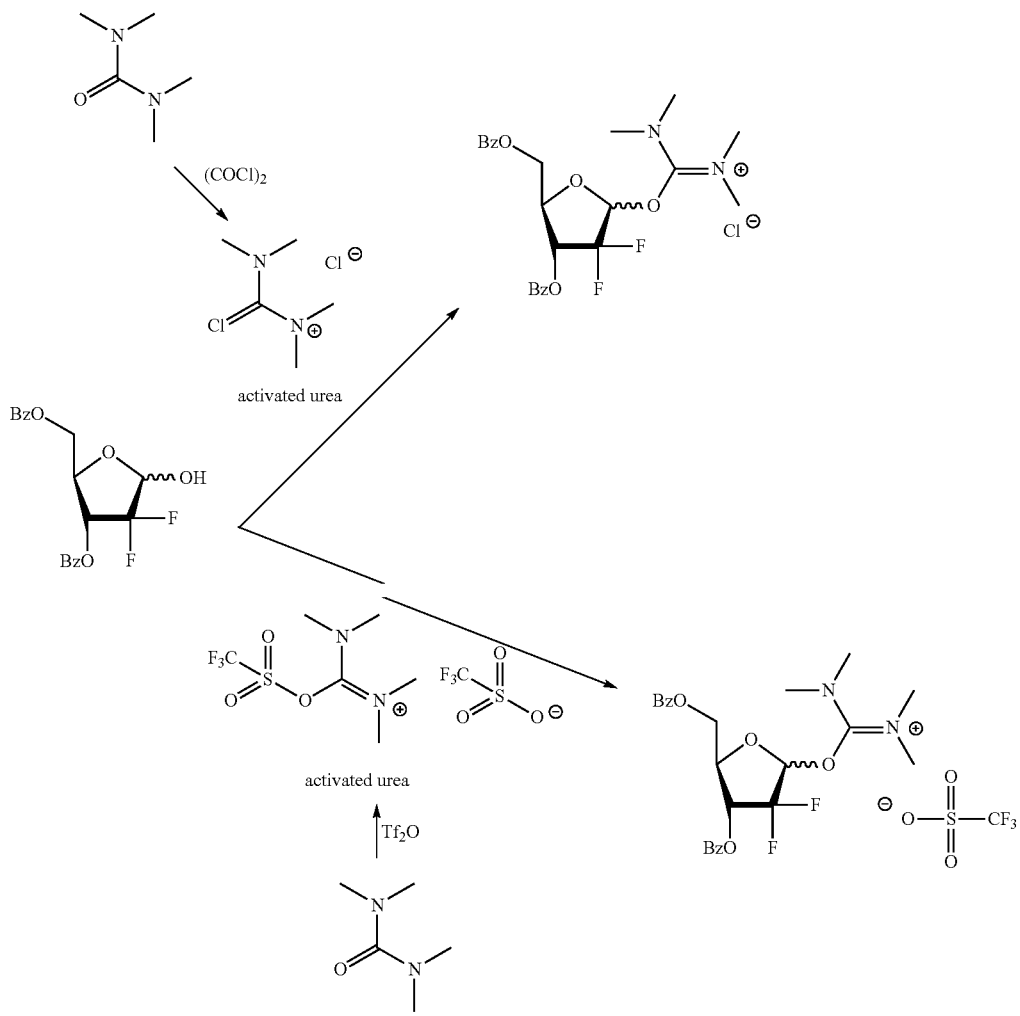

The fourth aspect of the present application is a process of making a 2-deoxy-2,2-difluoro-D-ribofuranosyl nucleoside of formula E

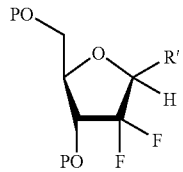

E wherein each P is independently a hydrogen or a hydroxyl protecting groups, and R' is a nucleobase residue. The process comprises:

converting a compound of formula (A) or salt thereof:

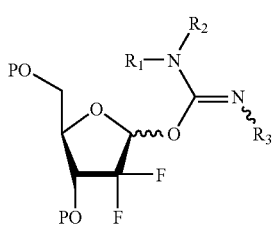

A wherein each of $R_1$, $R_2$, and $R_3$ independently represents hydrogen, alkyl, aryl, acyl, sulfonyl, or silyl; P is as defined above; to the nucleoside of formula E. Preferably, the converting step comprises: condensing the compound of formula (A) or salt thereof with an optionally protected nucleobase.

If the compound of formula (A) per se is involved in the condensing step, then an activating agent such as a Brønsted or Lewis acid or alkylating agent is preferably used to facilitate the reaction. If the salt of the compound of formula (A), in particular a salt with formula (B) as defined above, is involved in the condensing step, then the process does not require any activating agent or alkylating agent.

The optionally protected nucleobase may be one of the following:

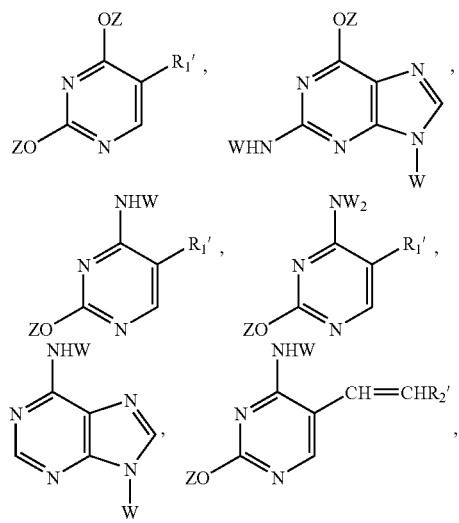

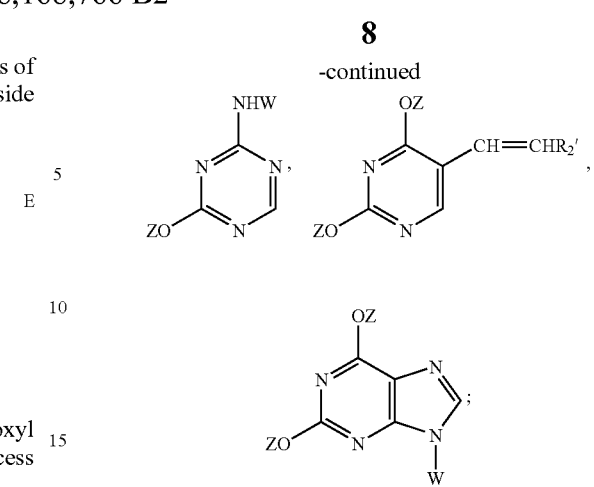

wherein Z is a hydroxyl protecting group, typically trimethylsilyl; W is an amino protecting group, typically trimethylsilyl; $R_1'$ is selected from the group consisting of hydrogen, alkyl, and halo; and $R_2'$ is selected from the group consisting of hydrogen, alkyl, and halo.

Preferably, R' in the above formula (E) may be any of the following:

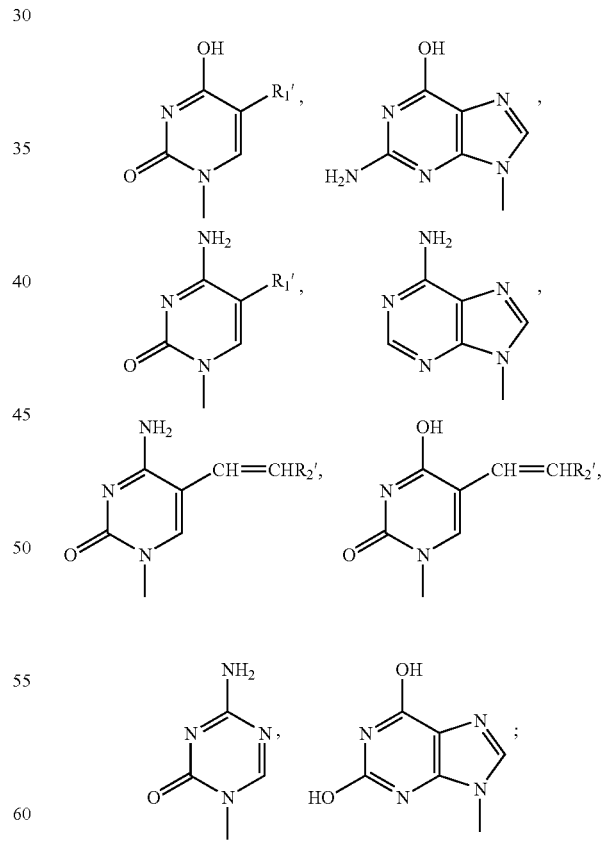

wherein $R_1'$ is selected from the group consisting of hydrogen, alkyl, and halo;

and $R_2'$ is selected from the group consisting of hydrogen, alkyl, and halo.

Alternatively and preferably, R' in the above formula (E) may be any of the following:

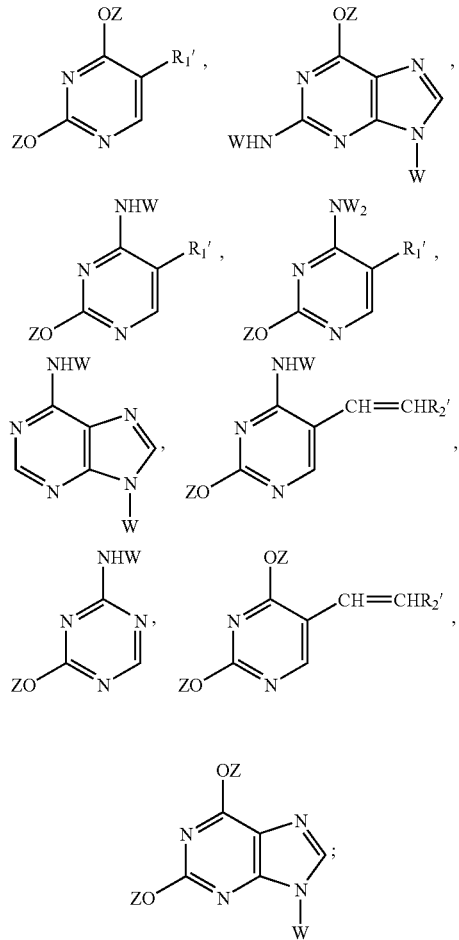

wherein Z is a hydroxyl protecting group; W is an amino protecting group; $R_1'$ is selected from the group consisting of hydrogen, alkyl, and halo; and $R_2'$ is selected from the group consisting of hydrogen, alkyl, and halo.

More preferably, the nucleoside made in the process of the present application is gemcitabine.

Preferably, the compound of formula (A) or salt thereof used as an intermediate to make a nucleoside is alpha-anomer enriched (i.e., the alpha-anomer to beta-anomer ratio is greater than 1:1), more preferably has an alpha-anomer to beta-anomer ratio of at least 2:1.

Compared to the methods reported by others, in accordance with the process of the present application, the compounds of Formulae A and B may be synthesized in an anomerically enriched form. Both can be synthesized in enriched alpha-anomer, as shown below. This is important, because many nucleoside products, such as gemcitabine, are desired to exist in a single anomeric isomer in the beta-anomeric form. Therefore, an alpha-anomer enriched Form A and B compound is desirable in making a beta-anomer enriched nucleoside, by use of an $S_N2$ (substitution nucleophilic second order reaction) reaction, in which the urea-based leaving group is stereo specifically substituted by a nucleobase.

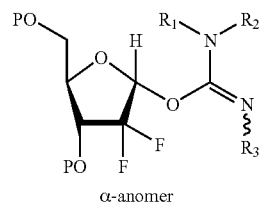

α-anomer

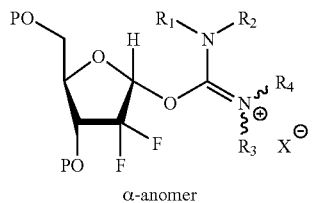

α-anomer

For example, in accordance with one embodiment of the present invention, synthesis of a compound of formula (A) where $R_1$ and $R_3$=cyclohexyl and $R_2$=hydrogen and P=Benzoyl yields a 6.9:1 ratio of the desired alpha-anomer to the undesired beta-anomer. The amount of enrichment also may depend on the specific type and amount of catalyst used (typically a metal salt), and specific $R_1$ and $R_3$ groups in the formula (A).

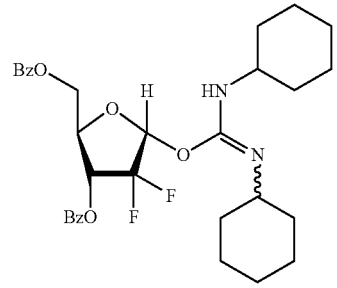

α-anomer

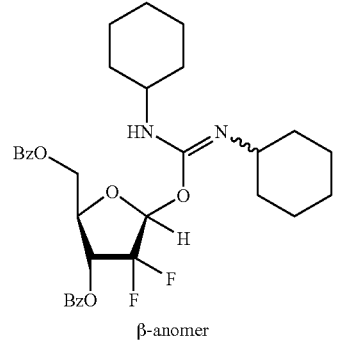

β-anomer

Ratio = 87:13

The alpha-anomer to the undesired beta-anomer ratio may be further improved by crystallisation. However, the crystallization is not required, since the process in accordance with an embodiment of the present application is capable of producing a satisfactory high ratio of the alpha-anomer to the undesired beta-anomer ratio.

For example, synthesis of a compound of formula (B) where $R_1$, $R_2$, $R_3$, $R_4$ methyl, X=OTf and P=benzoyl yields a 3:1 ratio of the desired alpha-anomer to the undesired beta-anomer. The reaction temperature at which this reaction is conducted may also influence the level of enrichment in the alpha-anomer.

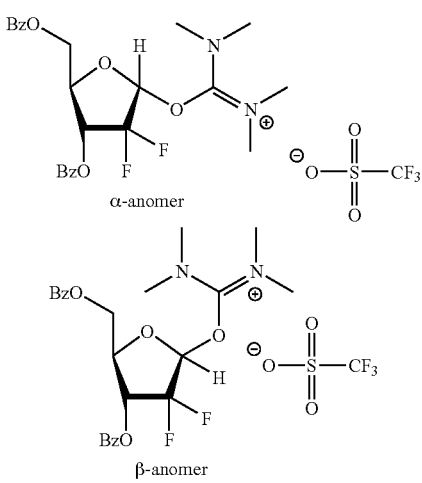

Ratio = 75:25

Since in accordance with an embodiment of the present application a significantly anomerically enriched form of a compound of formula (A) or (B), in particular the compound of formula (A) can be obtained, enrichment through crystallization or a process of synthesizing an sugar intermediate at a low temperature is not required.

In addition, the compound of formula (B) is much more reactive than those intermediates reported by others, because the compound of formula (B) has been activated by virtue of a positive charge on the leaving group. Therefore, unlike many methods reported by others, when using the compound of formula (B) as the intermediate to make a nucleoside, an external catalyst is not required to facilitate the reaction.

The various features of novelty which characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENTS

The following examples are provided to illustrate, but not to limit, the present invention.

Example 1

Synthesis of 2'-deoxy-2',2'-difluoro-3',5'-di-O-benzoyl-cytidine hydrochloride (protected gemcitabine, compound VI) from 1,1,3,3-tetramethyl-2-(2'-deoxy-2',2'-difluoro-3',5'-di-O-benzoyl-D-ribofuranosyl)-isouronium chloride (compound IIa)

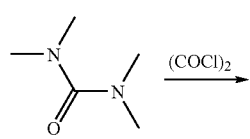

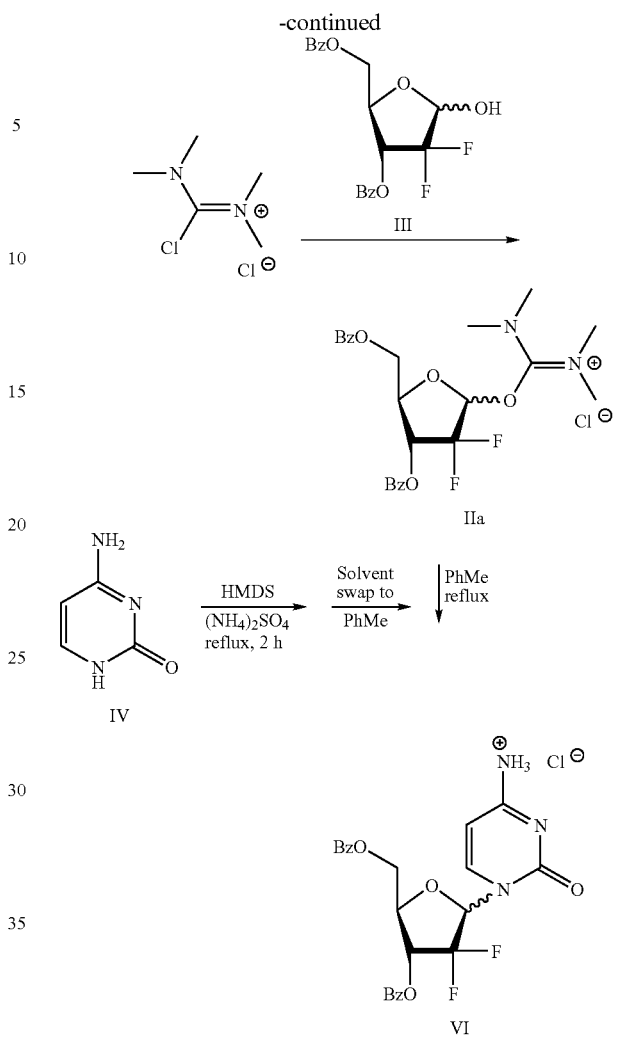

Step A

Preparation of 1,1,3,3-tetramethyl-2-chloro-isouronium chloride

Oxalyl chloride (15 mL, 0.175 mol) was added into a stirred solution of N,N,N',N'-tetramethylurea (12.2 g, 0.105 mol) in anhydrous 1,2-dicholoroethane (DCE; 150 mL) at room temperature. The reaction mixture was then heated to 60° C. and maintained at that temperature for 1.5 hours. Additional oxalyl chloride (10 mL, 0.115 mol) was added into the above solution and the mixture was stirred for 1 hour. The reaction was cooled to room temperature. The solid product was isolated and washed with DCE giving 95% $^1$H NMR purity product as a white solid. $^1$H NMR (300 MHz, CDCl$_3$) δ 3.59 (12H, s).

Step B

Preparation of 1,1,3,3-tetramethyl-2-(2'-deoxy-2',2'-difluoro-3',5'-di-O-benzoyl-D-ribofuranosyl)-isouronium chloride (compound IIa)

N,N-Diisopropylethylamine (DIPEA, 1.72 mL, 10.4 mmol) was added dropwise into a stirred solution of 1,1,3,3- tetramethyl-2-chloro-isouronium chloride (2.05 g, 11.4 mmol) and 2-deoxy-2,2-difluoro-3,5-di-O-benzoyl-ribofuranose (compound III, 3.92 g, 10.4 mmol) in anhydrous DCE (39 mL) at 0° C. The mixture was stirred at 0° C. until the reaction was complete. A small sample of the reaction mixture was evaporated and analysed by $^1$H NMR spectroscopy showing a mixture of the α- and β-anomers: $^1$H NMR (300 MHz, CDCl$_3$): δ3.09 (12H, s), 3.28 (12H, s), 4.41 (1H, dd, J=12.6 Hz, J=3.9 Hz), 4.63 (3H, m), 4.86 (1H, m), 4.95 (1H, dd, J=12.6 Hz, J=2.1 Hz), 5.52 (1H, dd, J=15.9 Hz, J=4.2 Hz), 5.85 (1H, m), 6.90 (1H, d, J=5.4 Hz), 6.98 (1H, d, J=5.7 Hz), 7.42 (8H, m), 7.57 (4H, m), 7.96 (8H, m).

Step C

Preparation of Compound VI

A mixture of cytosine (8.89 g, 80 mmol), 1,1,1,3,3,3-hexamethyldisilazane (HMDS, 88.9 ml) and (NH$_4$)$_2$SO$_4$ (0.009 g) was heated to reflux. After clarification of the reaction solution, the heating was continued for a further 2 hours. The HMDS was distilled under vacuum at 60-80° C. The residue was dissolved in toluene and this too was distilled. The residue, silylated cytosine, was diluted with toluene (9 mL) and was heated to reflux. Then a DCE solution of compound IIa (4 mmol) prepared above was added to the refluxing toluene solution of the silylated cytosine. The reaction was complete after 1 hour as shown by HPLC analysis (ZORBAX SB-C18, 5 μm, 4.6×150 mm, flow rate=1.5 mL/min, detection at 232 nm, 0.05% H$_3$PO$_4$ in H$_2$O:MeCN, 0 min 90:10; 5-26 min 50:50; 27-35 min 20:80), $R_{T(\alpha\text{-anomer } VI)}$=6.7 min, $R_{T(\beta\text{-anomer } VI)}$=6.9 min. The solution was treated with aqueous HCl and the protected nucleoside HCl salt (compound VI) was isolated by filtration.

$^1$H NMR (300 MHz, DMSO-d$_6$): δ 4.66 (2H, m), 4.72 (2H, m), 4.85 (1H, m), 5.24 (1H, m), 5.79 (1H, m), 6.00 (1H, d, J=7.5 Hz), 6.24 (2H, m), 6.42 (1H, t, J=8.7 Hz), 6.54 (1H, t, J=6.9 Hz), 7.56 (8H, m), 7.70 (4H, m), 7.98 (8H, m), 8.05 (1H, m), 8.19 (1H, d, J=7.5 Hz) 8.60 (1H, s), 8.88 (2H, s), 9.70 (1H, s), 10.01 (2H, s).

The protected nucleoside HCl salt may be converted into gemcitabine hydrochloride using any suitable method, such as those reported in the art.

Example 2

Synthesis of 2'-deoxy-2',2'-difluoro-3',5'-di-O-benzoyl-cytidine hydrochloride (protected gemcitabine, compound VI) from 1,1,3,3-tetramethyl-2-(2'-deoxy-2',2'-difluoro-3',5'-di-benzoyl-D-ribofuranosyl)-isouronium triflate (compound IIb)

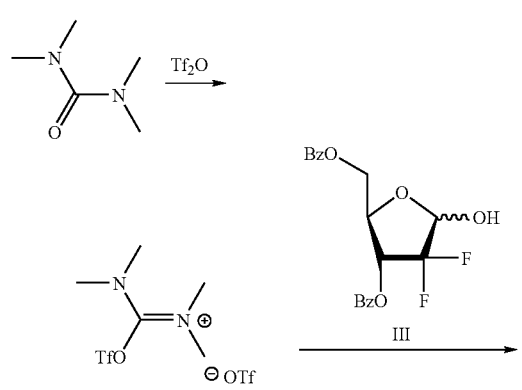

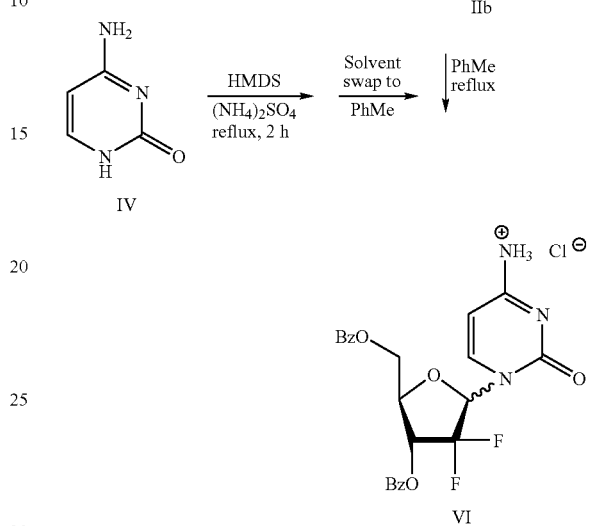

Step A

Preparation of 1,1,3,3-tetramethyl-2(trifluoromethylsulfonyl)-isouronium triflate (compound IIb)

Triflic anhydride (1 mL, 6.03 mmol) was added dropwise into a stirred solution of N,N,N',N'-tetramethylurea (0.74 mL, 6.03 mmol) in anhydrous DCE (5 mL) at 0° C. The reaction mixture was then warmed to room temperature and stirred for about 3 hours. The resulting solution was used directly in the next step. $^1$H NMR analysis of a small sample showed: $^1$H NMR (300 MHz, CDCl$_3$) δ 3.29 (12H, s).

Step B

Preparation of 1,1,3,3-tetramethyl-2-(2'-deoxy-2',2'-difluoro-3',5'-di-O-benzoyl-D-ribofuranosyl)-isouronium triflate (compound IIb)

A DCE solution of compound III (1.59 g, 4.2 mmol, in 3.5 mL of anhydrous DCE) was added dropwise to a stirred solution of DIPEA (0.9 mL, 5.4 mmol) and the above prepared DCE solution of 1,1,3,3-tetramethyl-2-(trifluoromethylsulfonyl)-isouronium triflate (4.2 mmol) at 0° C. The reaction mixture was then warmed to room temperature and was stirred until the reaction was complete. A small sample of the reaction mixture was evaporated and analysed by $^1$H NMR spectroscopy: $^1$H NMR (300 MHz, CDCl$_3$): δ 3.04 (12H, s), 3.21 (12H, s), 4.47 (1H, dd, J=12.8 Hz, J=4.0 Hz), 4.67 (3H, m), 4.96 (1H, m), 5.04 (1H, dd, J=12.8 Hz, J=2.0 Hz), 5.60 (1H, dd, J=16.0, J=4.0 Hz), 5.93 (1H, q, J=7.2 Hz), 6.25 (1H, d, J=6.0 Hz), 6.29 (1H, d, J=5.2 Hz), 7.46 (8H, m), 7.60 (4H, m), 8.02 (8H, m).

The DIPEA triflic acid salt could be removed by aqueous washing.

Step B

Preparation of α-Anomer Enriched Compound IIb

Triethylamine (0.58 mL, 4.2 mmol) was added to a DCE solution of compound III (1.59 g, 4.2 mmol, in 3.5 mL of anhydrous DCE) and stirred for more than 15 minutes. The mixture was then added dropwise to a stirred solution of DIPEA (0.9 mL, 5.4 mmol) and the above prepared 1,1,3,3-tetramethyl-2-(trifluoromethylsulfonyl)-isouronium triflate (4.2 mmol) DCE solution at 0° C. The reaction mixture was then warmed to room temperature and was stirred until the reaction was complete. A small sample of the reaction mixture was evaporated and analysed by 1H NMR spectroscopy showing that the α-anomer to β-anomer ratio was 3:1.

Step C

Preparation of Compound VI

A mixture of cytosine (10.3 g, 93 mmol), HMDS, 103 mL) and $(NH_4)_2SO_4$ (0.04 g) was heated to reflux. After clarification of the reaction solution, the heating was continued for a further 2 hours. The HMDS was distilled under vacuum at 60-80° C. The residue was dissolved in toluene (9 mL) and this too was distilled. The residue, silylated cytosine, was diluted with toluene (9 mL) and was heated to reflux. Then a DCE solution of compound IIb (3.1 mmol) prepared above was added to the refluxing toluene solution of the silylated cytosine. The reaction was complete after 1 hour as shown by HPLC analysis. The solution was treated with aqueous HCl and the protected nucleoside HCl salt (compound VI) was isolated by filtration. Analysis data for this compound is reported above.

The protected nucleoside HCl salt may be converted into gemcitabine hydrochloride using any suitable method, such as those reported in the art.

Example 3

Synthesis of 2'-deoxy-2',2'-difluoro-3',5'-di-O-benzoyl-cytidine hydrochloride (protected gemcitabine, compound VI) from O-(2'-deoxy-2',2'-difluoro-3',5'-di-O-benzoyl-D-ribofuranosyl)-N,N-dicyclohexylcarbamimidate (compound IIc)

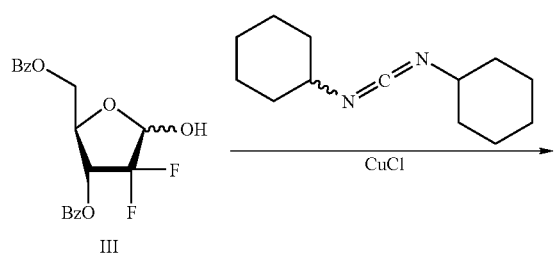

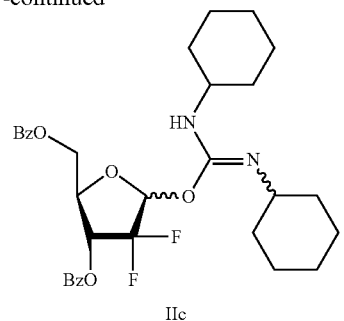

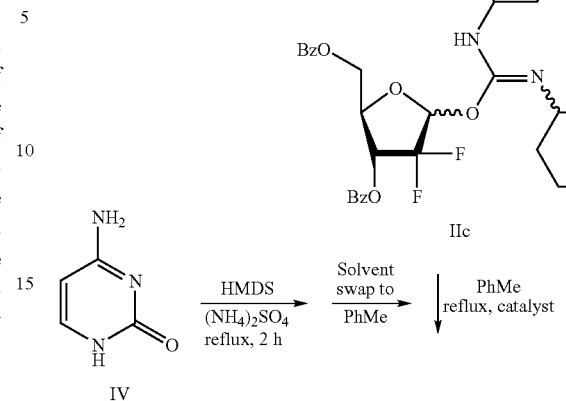

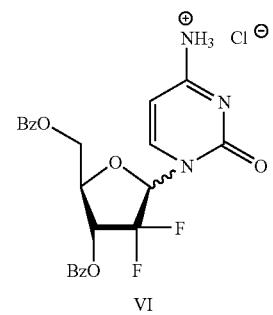

Step A

Preparation of O-(2'-deoxy-2',2'-difluoro-3',5'-di-O-benzoyl-D-ribofuranosyl)-N,N-dicyclohexylcarbamimidate (compound IIc)

To a mixture of DCC(N,N'-dicyclohexylcarbodiimide, 43.6 g, 0.212 mol), 2-deoxy-2,2-difluoro-3,5-di-O-benzoyl-ribofuranose (compound III; 40 g, 0.106 mol) in DMF (80 mL) at room temperature was added CuCl (2.3 g, 0.048 mol). Then was stirred for more than 24 hours. Once the reaction was complete (as indicated by TLC analysis) the mixture was washed with aqueous $NH_4OH$ followed by washed. The water washings were back extracted with DCM three times and the combined DCM fractions were evaporated to give compound IIc as colourless oil with 95% HPLC purity (Column:ZORBAX SB-C18, 5 um, 4.6×150 mm, Mobile Phase: 5 mM $KH_2PO_4$ (pH 8.70, $H_3PO_4$):MeCN, 0 min 90:10; 5-26 min 50:50; 27-35 min 20:80), Flow rate 1.5 mL/min, Detection at 232 nm, $R_{T(\beta-anomer)}$=32 min, $R_{T(\alpha-anomer)}$=34 min) as an approximately 7:1 mixture (based on $^1$H NMR and HPLC analysis) of the α-anomer and β-anomer respectively. $^1$H NMR (300 MHz, $CDCl_3$): δ 0.88~1.92 (m, 21H), 2.83 (s, 1H), 3.20 (m, 1H), 3.45 (m, 1H), 3.60 (m, 1H), 4.58 (m, 2H), 4.68 (m, 2H), 5.45 (d, J=16.2 Hz, 1H), 5.80 (m, 1H), 6.58 (d, J=7.8 Hz, 1H), 6.72 (d, J=7.2 Hz, 1H), 7.45 (m, 4H), 7.60 (m, 2H), 8.08 (m, 4H). API-ES: m/z 585 (MH$^+$). IR $\lambda_{Max}^{KBr}$:1044.61 cm$^{-1}$, 1732.93 cm$^{-1}$, 2923.82 cm$^{-1}$.

Step B

Preparation of Compound VI from Compound IIc

Using TMSOTf as catalyst: To a solution of O-(2'-deoxy-2',2'-difluoro-3',5'-di-O-benzoyl-D-ribofuranosyl)-N,N'-dicyclohexylcarbamimidate (compound IIc; 1.5 g, 2.57 mmol)

in toluene (15 mL) was added trimethylsilyl triflate (TMSOTf; 0.14 g, 0.64 mmol). After stirring for 15 minutes silylated cytosine prepared as described above (13.1 g, 51.4 mmol) was and the reaction mixture was stirred at 90° C. until compound IIc was consumed, as determined by HPLC analysis. 1N aqueous HCl (5 mL) and DCM (30 mL) was added and was stirred for at least 1 hour. The mixture was filtered, the solid was washed with 1N aqueous HCl (5 mL) and DCM (5 mL), dried under vacuum at 45° C. O-(2'-deoxy-2',2'-difluoro-3',5'-di-O-benzoyl-D-ribofuranosyl)-N,N'-dicyclohexylcarbamimidate (compound IIc; 1.5 g, 2.57 mmol) was dissolved in toluene (15 mL), trimethylsilyl triflate (TMSOTf; 0.14 g, 0.64 mmol) or triflic acid (TfOH; 0.096 g, 0.64 mmol) were added. After stirring for 15 minutes silylated cytosine prepared as described above (13.1 g, 51.4 mmol) was charged at room temperature. The reaction mixture was stirred at 90° C. until compound IIc was consumed, as determined by HPLC analysis. Analysis data for this compound is reported above.

TfOH could be used in place of TMSOTf in the above experiment.

Example 4

Synthesis of 2'-deoxy-2',2'-difluoro-3',5'-di-O-benzoyl-cytidine hydrochloride (protected gemcitabine, compound VI) from O-(2'-deoxy-2',2'-difluoro-3',5'-di-O-benzoyl-D-ribofuranosyl)-N,N'-dicyclohexyl-N-mesyl-carbamimidate (compound IIc-Ms)

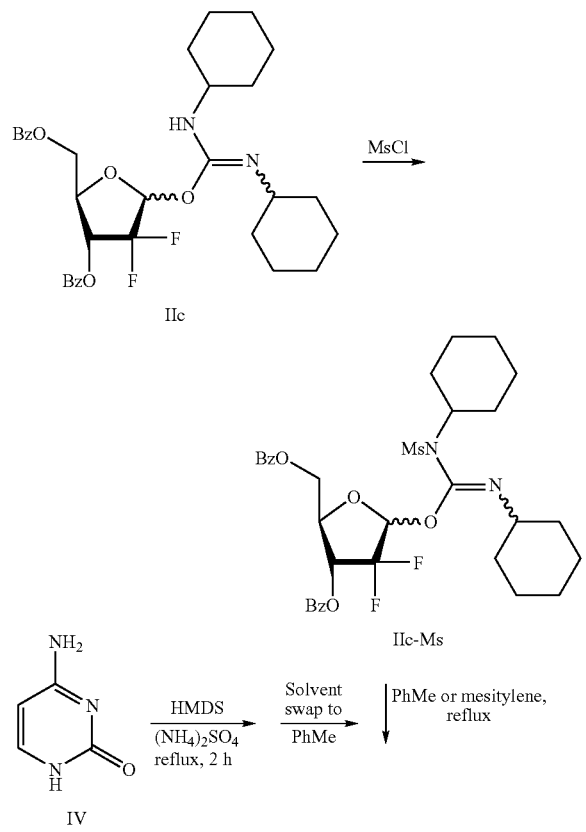

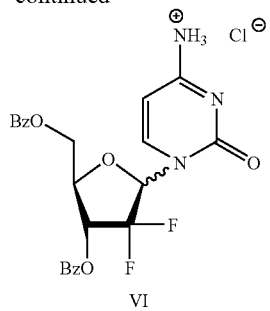

VI

Step A

Preparation of O-(2'-deoxy-2',2'-difluoro-3',5'-di-O-benzoyl-D-ribofuranosyl)-N,N'-dicyclohexyl-N-mesyl-carbamimidate (compound Ic-Ms)

O-(2'-deoxy-2',2'-difluoro-3',5'-di-O-benzoyl-D-ribofuranosyl)-N,N'-dicyclohexylcarbamimidate (compound IIc; 6 g, 10.3 mmol) was dissolved in anhydrous DCM (30 mL) at room temperature. DIPEA (5.03 g, 41.2 mmol) and 4-(N,N-dimethylamino)pyridine (DMAP; 0.1 g) was added and the mixture was stirred at 0° C. for 15 minutes. Methanesulfonyl chloride (MsCl; 3.53 g, 30.9 mmol) was added dropwise to the stirred solution at about 0° C. for more than 2 hours until the reaction complete as judged by TLC analysis. The product was washed with water and the product was isolated as colorless oil with 80% HPLC purity by evaporation of the organic solvent. The product was an approximately 5:1 mixture of the α- and β-anomers, respectively.

$^1$H NMR (CDCl$_3$) δ 1.34~1.95 (m, 21H), 3.18 (m, 2H), 3.57 (m, 2H), 4.55 (m, 2H), 4.72 (m, 2H), 5.45 (dd, J=3.9 Hz, J=4.5 Hz, 1H), 5.75 (m, 1H), 6.40 (d, J=7.8 Hz, 1H), 6.45 (d, J=7.2 Hz, 1H).

Step B

Preparation of Compound VI from Compound IIc-Ms

A mixture of O-(2'-deoxy-2',2'-difluoro-3',5'-di-O-benzoyl-D-ribofuranosyl)-N,N'-dicyclohexyl-N-mesyl-carbamimidate (compound IIc-Ms; 1.5 g, 2.03 mmol) and silylated cytosine (10.35 g, 40.6 mmol) prepared as described above in mesitylene (15 mL) was stirred at 110° C. to 130° C. for more than 24 hours. HPLC analysis showed that a mixture of the α- and β-anomers of compound VI were formed in this reaction but the product was not isolated.

The invention is not limited by the embodiments described above which are presented as examples only but can be modified in various ways within the scope of protection defined by the appended patent claims.

We claim:
1. A process of making a nucleoside of formula E

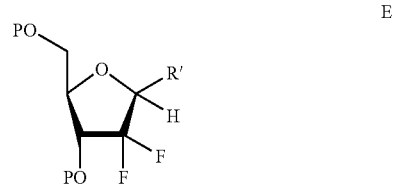

wherein each P is independently a hydrogen or a hydroxyl protecting groups, and R' is a nucleobase residue; the process comprises:

converting a compound of formula (A) or salt thereof:

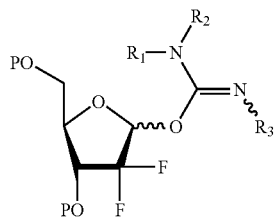

wherein each of $R_1$, $R_2$, and $R_3$ independently represents hydrogen, alkyl, aryl, acyl, sulfonyl, or silyl; P is as defined above; to the nucleoside of formula E.

2. The process of claim 1 wherein the converting step comprises: condensing the compound of formula (A) or salt thereof with an optionally protected nucleobase.

3. The process of claim 2 wherein the optionally protected nucleobase is one of the following:

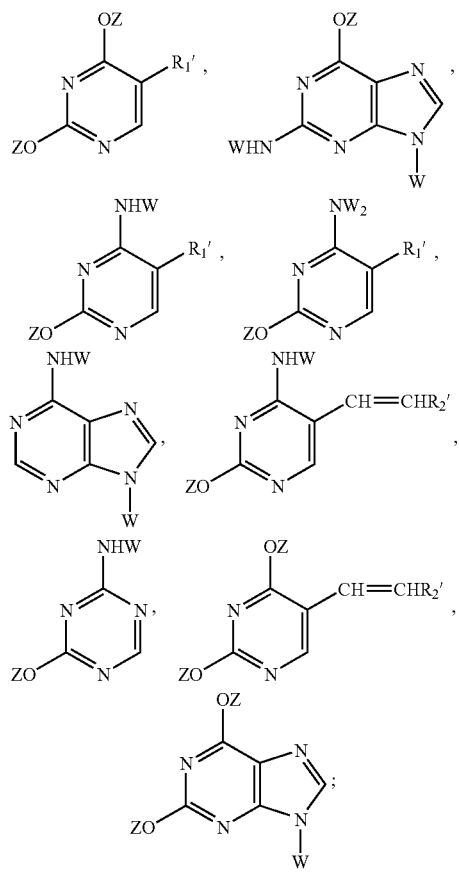

wherein Z is a hydroxyl protecting group; W is an amino protecting group; $R_1'$ is selected from the group consisting of hydrogen, alkyl, and halo; and $R_2'$ is selected from the group consisting of hydrogen, alkyl, and halo.

4. The process of claim 1 wherein R' is any of the following:

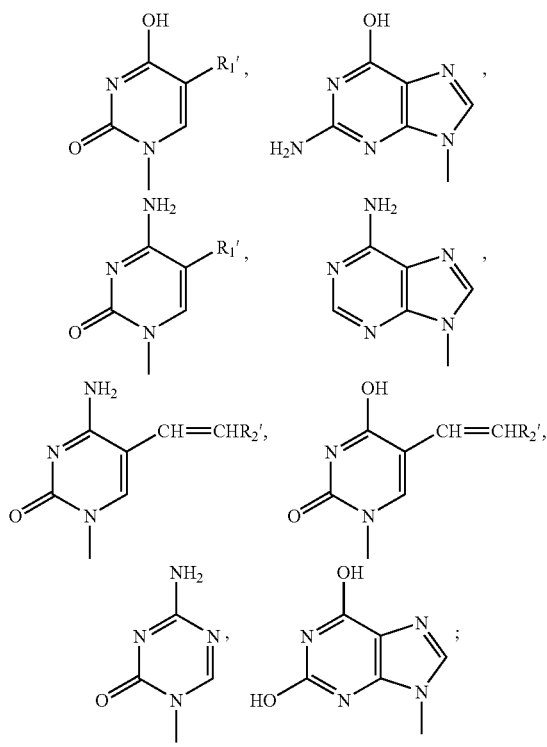

wherein $R_1'$ is selected from the group consisting of hydrogen, alkyl, and halo; and $R_2'$ is selected from the group consisting of hydrogen, alkyl, and halo.

5. The process of claim 1 wherein R' is any of the following:

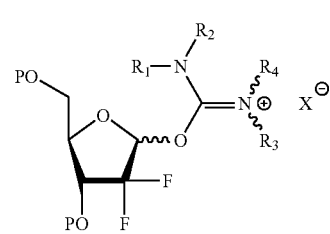

wherein Z is a hydroxyl protecting group; W is an amino protecting group; $R_1'$ is selected from the group consisting of hydrogen, alkyl, and halo; and $R_2'$ is selected from the group consisting of hydrogen, alkyl, and halo.

6. The process of claim 1 wherein the nucleoside is gemcitabine.

7. The process of claim 1 wherein the hydroxy protecting group is selected from the group consisting of benzoyl, 4-phenylbenzoyl, 4-bromobenzoyl, 4-chlorobenzoyl, formyl, acetyl, 2-chloroacetyl, benzyl, diphenylmethyl, triphenyl methyl, 4-nitrobenzyl, phenoxycarbonyl, tertiary-butyl, methoxymethyl, tetrahydropyranyl, allyl, tetrahydrothienyl, 2-methoxethoxy methyl, methoxy acetyl, phenoxy acetyl, isobutyryl, ethoxy carbonyl, benzyloxy carbonyl, mesyl, trimethylsilyl, isopropyl dimethylsilyl, methyldiisopropyl silyl, triisopropyl silyl, and tertiary-butyldimethyl silyl.

8. The process of claim 1 wherein each of $R_1$ and $R_3$ independently represents an alkyl group or an aryl group, and $R_2$ represents hydrogen or a sulfonyl group.

9. The process of claim 1 wherein each of $R_1$ and $R_3$ independently represents a cyclohexyl group, and $R_2$ represents hydrogen or sulfonyl.

10. The process of claim 1 wherein the salt of the compound of formula (A) is a compound having formula (B):

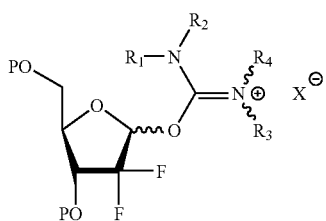

B wherein each of $R_1$, $R_2$, $R_3$, and P is as defined in claim 1; $R_4$ is hydrogen, alkyl, aryl, acyl, sulfonyl, or silyl; and X represents a non-nucleophilic counter ion.

11. The process of claim 10 wherein X is selected from the group consisting of halide, sulfonate, carboxylate, $^-PF_6$, and $^-BF_4$.

12. The process of claim 10 wherein each of $R_1$, $R_2$, $R_3$, $R_4$ represents methyl, and X represents chloride or triflate.

13. The process of claim 10 wherein the compound of formula B is prepared by a process comprising:
reacting a 3,5-di-O-protected 2-deoxy-2,2-difluoro-D-ribose with an activated urea-derived compound having a formula D

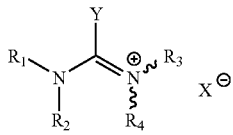

D where each of $R_1$, $R_2$, $R_3$, $R_4$, and X is defined as above, Y is selected from the group consisting of halo, sulfonate, carboxylate, and trifluoromethanesulfonate in an organic solvent in the presence of a non-nucleophilic amine base.

14. The process of claim 1 wherein the compound formula (A) or salt thereof is prepared by a process comprising:
reacting a 3,5-di-O-protected 2-deoxy-2,2-difluoro-D-ribose with a carbodiimide compound of formula C

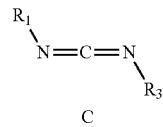

C in an organic solvent in the presence of a catalyst.

15. The process of claim 14 wherein the catalyst is a metal salt.

16. The process of claim 14 wherein the catalyst is a cuprate salt.

17. The process of claim 14 wherein $R_2$ represents sulfonyl, and the process comprises a further step of reacting the product of the reaction of the 3,5-di-O-protected 2-deoxy-2,2-difluoro-D-ribose and the carbodiimide compound of formula C with a sulfonating agent in an organic solvent in the presence of an amine base.

18. The process of claim 17 wherein the sulfonating agent is a sulfonic anhydride or sulfonyl halide.

19. The process of claim 14 comprising a further step of converting the reaction product of the 3,5-di-O-protected 2-deoxy-2,2-difluoro-D-ribose and the carbodiimide compound of formula C to the salt of the compound of formula (A).

* * * * *

UNITED STATES PATENT AND TRADEMARK OFFICE
CERTIFICATE OF CORRECTION

PATENT NO. : 8,168,766 B2
APPLICATION NO. : 12/550548
DATED : May 1, 2012
INVENTOR(S) : Julian Paul Henschke et al.

It is certified that error appears in the above-identified patent and that said Letters Patent is hereby corrected as shown below:

IN THE CLAIMS:
Column 20, at claim 5, lines 37-48, the formula should appear as follows:

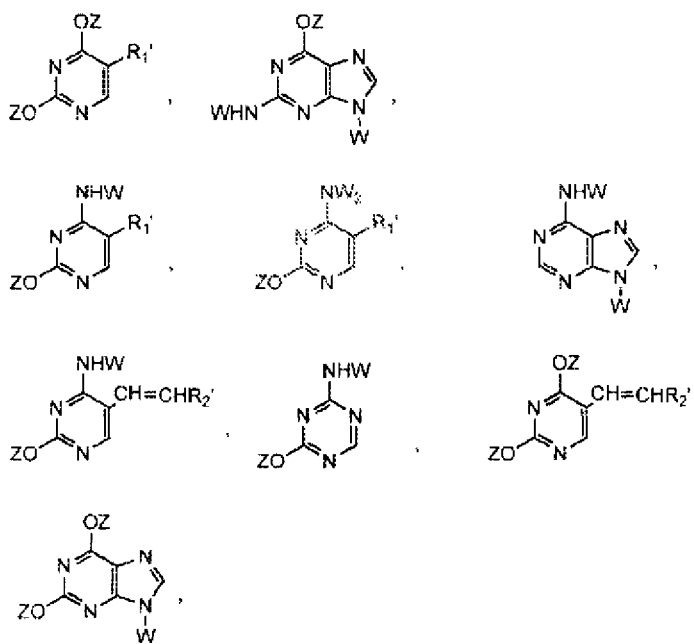

Signed and Sealed this
Twelfth Day of June, 2012

David J. Kappos
*Director of the United States Patent and Trademark Office*